United States Patent
Lin et al.

(10) Patent No.: US 12,203,140 B2
(45) Date of Patent: Jan. 21, 2025

(54) METHODS FOR EARLY PREDICTION, TREATMENT RESPONSE, RECURRENCE AND PROGNOSIS MONITORING OF BREAST CANCER

(71) Applicant: EG BioMed Co., Ltd., Taipei (TW)

(72) Inventors: Ruo-Kai Lin, New Taipei (TW); Chin-Sheng Hung, Taipei (TW); Sheng-Chao Wang, New Taipei (TW); Yu-Mei Chung, Miaoli County (TW); Chih-Ming Su, New Taipei (TW)

(73) Assignee: EG BIOMED CO., LTD., Taipei (TW)

( * ) Notice: Subject to any disclaimer, the term of this patent is extended or adjusted under 35 U.S.C. 154(b) by 0 days.

(21) Appl. No.: 17/053,688

(22) PCT Filed: May 8, 2019

(86) PCT No.: PCT/US2019/031292
§ 371 (c)(1),
(2) Date: Nov. 6, 2020

(87) PCT Pub. No.: WO2019/217537
PCT Pub. Date: Nov. 14, 2019

(65) Prior Publication Data
US 2021/0189500 A1    Jun. 24, 2021

Related U.S. Application Data

(60) Provisional application No. 62/668,435, filed on May 8, 2018.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| | | |
|---|---|---|
| 2008/0311570 A1 | 12/2008 | Lai |
| 2014/0045915 A1* | 2/2014 | Skog ............... C12Q 1/6886 514/44 A |
| 2014/0113286 A1 | 4/2014 | Chan et al. |
| 2017/0283886 A1 | 10/2017 | Clark et al. |

FOREIGN PATENT DOCUMENTS

| | | |
|---|---|---|
| EP | 2828405 B1 | 6/2017 |
| WO | 2012088298 A2 | 6/2012 |
| WO | 2016071477 A1 | 5/2016 |
| WO | 2017201606 A1 | 11/2017 |
| WO | 2019108626 A1 | 6/2019 |

OTHER PUBLICATIONS

Michels, Karin (The promises and challenges of epigenetic epidemiology. Experimental Gerontology 2010 vol. 45 pp. 297-301) (Year: 2010).*
Sehl (Breast Cancer Res Treat Mar. 2017 vol. 164 p. 209-219) (Year: 2017).*
International Search Report and Written Opinion dated Sep. 13, 2019 for International Patent Application No. PCT/US19/31292.
Akulenko, Rusian and Helms, Volkhard, "DNA co-methylation analysis suggests novel functional associations between gene pairs in breast cancer samples," Human Molecular Genetics, (2013), vol. 22, No. 15, pp. 3016-3022.
Office Action received in Japan Patent Application No. 2020-562713 issued on Jun. 28, 2023.

* cited by examiner

*Primary Examiner* — Katherine D Salmon
(74) *Attorney, Agent, or Firm* — Prosyla Group PC

(57) ABSTRACT

The present invention discloses a set of novel epigenetic biomarkers for early prediction, treatment response, recurrence and prognosis monitoring of a breast cancer. Aberrant methylation of the genes can be detected in tumor tissues and plasma samples from breast cancer patients but not in normal healthy individual. The present disclosure also discloses primers and probes used herein.

6 Claims, 12 Drawing Sheets
Specification includes a Sequence Listing.

A

B

SEQUENCE LISTING

<160> NUMBER OF SEQ ID NOS: 19

<210> SEQ ID NO 1

```
<211> LENGTH: 26
<212> TYPE: DNA
<213> ORGANISM: artificial sequence
<220> FEATURE:
<223> OTHER INFORMATION: synthetic polynucleotide

<400> SEQUENCE: 1 gtttttttatt tttgtcgttg cgtttc                                        26

<210> SEQ ID NO 2
<211> LENGTH: 20
<212> TYPE: DNA
<213> ORGANISM: artificial sequence
<220> FEATURE:
<223> OTHER INFORMATION: synthetic polynucleotide

<400> SEQUENCE: 2
cgaaaaaaat tccccgacct                                                20

<210> SEQ ID NO 3
<211> LENGTH: 25
<212> TYPE: DNA
<213> ORGANISM: artificial sequence
<220> FEATURE:
<223> OTHER INFORMATION: synthetic polynucleotide

<400> SEQUENCE: 3
gtagttgttt tcggttttcg gtttc                                          25

<210> SEQ ID NO 4
<211> LENGTH: 26
<212> TYPE: DNA
<213> ORGANISM: artificial sequence
<220> FEATURE:
<223> OTHER INFORMATION: synthetic polynucleotide

<400> SEQUENCE: 4
tactatcgcc gaccttatta aaaacg                                         26

<210> SEQ ID NO 5
<211> LENGTH: 20
<212> TYPE: DNA
<213> ORGANISM: artificial sequence
<220> FEATURE:
<223> OTHER INFORMATION: synthetic polynucleotide

<400> SEQUENCE: 5
gagatagggc ggagtttttc                                                20

<210> SEQ ID NO 6
<211> LENGTH: 22
<212> TYPE: DNA
<213> ORGANISM: artificial sequence
<220> FEATURE:
<223> OTHER INFORMATION: synthetic polynucleotide

<400> SEQUENCE: 6
cttaaccgcg atactaaacg tt                                             22

<210> SEQ ID NO 7
<211> LENGTH: 25
<212> TYPE: DNA
<213> ORGANISM: artificial sequence
<220> FEATURE:
<223> OTHER INFORMATION: synthetic polynucleotide

<400> SEQUENCE: 7
```
gagtgtagtt gatagtaggt acggc                              25

<210> SEQ ID NO 8
<211> LENGTH: 30
<212> TYPE: DNA
<213> ORGANISM: artificial sequence
<220> FEATURE:
<223> OTHER INFORMATION: synthetic polynucleotide

<400> SEQUENCE: 8
gtaaatttac taaaaaaata aaaaaaccgt                          30

<210> SEQ ID NO 9
<211> LENGTH: 25
<212> TYPE: DNA
<213> ORGANISM: artificial sequence
<220> FEATURE:
<223> OTHER INFORMATION: synthetic polynucleotide

<400> SEQUENCE: 9
ttttattggt ttttcgtaag tatcg                              25

<210> SEQ ID NO 10
<211> LENGTH: 25
<212> TYPE: DNA
<213> ORGANISM: artificial sequence
<220> FEATURE:
<223> OTHER INFORMATION: synthetic polynucleotide

<400> SEQUENCE: 10
cataacaaca acgtacctct acgtc                              25

<210> SEQ ID NO 11
<211> LENGTH: 20
<212> TYPE: DNA
<213> ORGANISM: artificial sequence
<220> FEATURE:
<223> OTHER INFORMATION: synthetic polynucleotide

<400> SEQUENCE: 11
tttagttgtt ggtcggaagc                                    20

<210> SEQ ID NO 12
<211> LENGTH: 21
<212> TYPE: DNA
<213> ORGANISM: artificial sequence
<220> FEATURE:
<223> OTHER INFORMATION: synthetic polynucleotide

<400> SEQUENCE: 12
cgacctcact aataaaacgc a                                  21

<210> SEQ ID NO 13
<211> LENGTH: 25
<212> TYPE: DNA
<213> ORGANISM: artificial sequence
<220> FEATURE:
<223> OTHER INFORMATION: synthetic polynucleotide

<400> SEQUENCE: 13
tgtcgcgttg gttttcgtt cgttt                               25

<210> SEQ ID NO 14
<211> LENGTH: 26
<212> TYPE: DNA

```
<213> ORGANISM: artificial sequence
<220> FEATURE:
<223> OTHER INFORMATION: synthetic polynucleotide

<400> SEQUENCE: 14
ctaaaacaac ccattacgaa aaacgc                                              26

<210> SEQ ID NO 15
<211> LENGTH: 24
<212> TYPE: DNA
<213> ORGANISM: artificial sequence
<220> FEATURE:
<223> OTHER INFORMATION: synthetic polynucleotide

<400> SEQUENCE: 15
ggtcgatgtt gtcgttcggg tgga                                                24

<210> SEQ ID NO 16
<211> LENGTH: 26
<212> TYPE: DNA
<213> ORGANISM: artificial sequence
<220> FEATURE:
<223> OTHER INFORMATION: synthetic polynucleotide

<400> SEQUENCE: 16
agggaggtcg agtagcggag agtgtg                                              26

<210> SEQ ID NO 17
<211> LENGTH: 23
<212> TYPE: DNA
<213> ORGANISM: artificial sequence
<220> FEATURE:
<223> OTHER INFORMATION: synthetic polynucleotide

<400> SEQUENCE: 17
tcgggagggg tcggtggttt gag                                                 23

<210> SEQ ID NO 18
<211> LENGTH: 24
<212> TYPE: DNA
<213> ORGANISM: artificial sequence
<220> FEATURE:
<223> OTHER INFORMATION: synthetic polynucleotide

<400> SEQUENCE: 18
gaagtgggcg ttcgtcgttt cgtt                                                24

<210> SEQ ID NO 19
<211> LENGTH: 149
<212> TYPE: DNA
<213> ORGANISM: artificial sequence
<220> FEATURE:
<223> OTHER INFORMATION: synthetic polynucleotide

<400> SEQUENCE: 19
cgcaggccag gccctctatt cctgtcgctg cgccccgcct tgccggctgc gtgtcacccc         60
cccccctgcc gcgctggctc cccgtccgtc ccaccagcct tgctgtcctg ggcaggccgg        120
ggaattcctc ccggttcctg gaaaaaaca                                          149
```

METHODS FOR EARLY PREDICTION, TREATMENT RESPONSE, RECURRENCE AND PROGNOSIS MONITORING OF BREAST CANCER

FIELD OF THE INVENTION

The invention relates to gene biomarkers for prediction of risk or susceptibility of a breast cancer and/or prognosis and malignancy of a breast cancer. Particularly, the invention detects a breast cancer and predicts risk of a breast cancer or susceptibility to a breast cancer and/or prognosis and malignancy of the breast cancer based on methylation of gene biomarkers.

BACKGROUND OF THE INVENTION

Cancer is a group of diseases involving abnormal cell growth with the potential to invade or spread to other parts of the body and is a leading cause of deaths worldwide.

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression.

US 20080311570A1A provides a method for screening cancer that comprises the following steps: (1) providing a test specimen; (2) detecting the methylation state of the CpG sequence in at least one target gene within the genomic DNA of the test specimen, wherein the target genes consist of SOX1, PAX1, LMX1A, NKX6-1, WT1 and ONECUT1; and (3) determining whether there is cancer or cancerous pathological change in the specimen based on the presence or absence of the methylation state in the target gene. WO 2016071477A1 relates to assessing the response of a cancer patient to a treatment by analyzing CpG methylation in the shox2 gene. EP2828405B1 provides methods for detecting colorectal neoplasia by evaluating multiple gene markers in blood or plasma and stool.

SUMMARY OF THE INVENTION

The present disclosure discloses a set of novel epigenetic biomarkers for early prediction, treatment response, recurrence and prognosis monitoring of a breast cancer. Aberrant methylation of the genes can be detected in tumor tissues and plasma samples from cancer patients but not in normal healthy individuals. The present disclosure also discloses primers and probes used herein.

In one embodiment, the present disclosure discloses a method for detecting the methylation status in a human subject who is in a need of detection of a breast cancer, comprising (a) providing a biological sample, and (b) assaying methylation status of epigenetic biomarkers in target DNA sequences GCM2 and ITPRIPL1 or fragments thereof, wherein the presence of hypermethylation in the DNA sequences of the human subject relative to a methylation state of a control is indicative of a breast cancer.

In one embodiment, the present disclosure discloses a method for detecting a predisposition to, or the incidence of, a breast cancer or predicting treatment response, prognosis or recurrence of a breast cancer in a human subject, comprising (a) providing a biological sample, and (b) assaying methylation status of epigenetic biomarkers in target DNA sequences GCM2 and ITPRIPL1 or fragments thereof, wherein the presence of hypermethylation in the DNA sequences of the human subject relative to a methylation state of a control is indicative of a predisposition to, or the incidence, poor treatment response, poor prognosis or recurrence of, the breast cancer.

In some embodiments, a GCM2 methylation specific probe and a ITPRIPL1 methylation specific probe are used to assay the methylation level of the target GCM2 and ITPRIPL1 DNA sequences or fragments thereof and a control DNA sequence in the sample.

In one embodiment, the present disclosure provides a method, comprising (a) providing a biological sample comprising GCM2 and ITPRIPL1 target DNA sequences or fragments thereof, and (b) assaying the methylation level of the target GCM2 and ITPRIPL1 DNA sequences or fragments thereof and a control DNA sequence in the sample using a GCM2 methylation specific probe and a ITPRIPL1 methylation specific probe, (c) measuring the relative methylation status of the target GCM2 and ITPRIPL1 DNA sequences or fragments thereof compared to a control DNA sequence to detect the presence of hypermethylated GCM2 and ITPRIPL1, (d) identifying the subject as in need of breast cancer treatment when the target DNA sequences GCM2 and ITPRIPL1 DNA sequences or fragments thereof of the human subject are hypermethylated relative to methylation of a control DNA sequence in said subject. The method can detect the methylation status in a human subject who is in need of detection of a breast cancer.

In one embodiment, the present disclosure provides a method, comprising (a) providing a biological sample comprising GCM2 and ITPRIPL1 target DNA sequences or fragments thereof, and (b) assaying the methylation level of the target GCM2 and ITPRIPL1 DNA sequences or fragments thereof and a control DNA sequence in the sample using a GCM2 methylation specific probe and a ITPRIPL1 methylation specific probe, (c) measuring the relative methylation status of the target GCM2 and ITPRIPL1 DNA sequences or fragments thereof compared to a control DNA sequence to detect the presence of hypermethylated GCM2 and ITPRIPL1, (d) identifying the subject as having a predisposition to, or the incidence, poor treatment response, or having poor prognosis or recurrence of, the breast cancer when the target DNA sequences GCM2 and ITRPIPL1 of the human subject are hypermethylated relative to a methylation state of a control DNA sequence in said subject.

In some embodiments, the biological sample is a tissue, cell, blood, urine, serum or plasma.

In some embodiments, methylation in the DNA sequences GCM2 and ITPRIPL1 or fragments thereof described herein that is about 64% higher than that of the control indicates a breast cancer. In a further embodiment, methylation in the DNA sequences GCM2 and ITPRIPL1 or fragments thereof that is about 69% higher than that of the control indicates a breast cancer. In a further embodiment, methylation in the DNA sequences GCM2 and ITPRIPL1 or fragments that is about 69% and about 80% higher than that of the control respectively indicates a breast cancer.

In some embodiments, a hypermethylation described herein is indicated when the methylation of the target DNA sequences in a human subject is at least 0.5, 1, 2 or 3 times higher than that in a control. In one embodiment, the hypermethylation is indicated when the methylation of the target DNA sequences in a human subject is at least 2 times higher than that in a control.

Certain embodiments of probes used in the methylation assay have a homology of about 85%, about 86%, about 87%, about 88%, about 89%, about 90%, about 91%, about 92%, about 93%, about 94%, about 95%, about 96%, about 97%, about 98%, about 99%, or higher percent to a sequence(s) selected from the group consisting of SEQ ID NOs:13 to 18. In some embodiments, the GCM2 methylation specific probe has a sequence with homology of at least 85% to SEQ ID NO:15, and a ITPRIPL1 methylation specific probe has a sequence with homology of at least 85% to SEQ ID NO:16. In some embodiments, the GCM2 methylation specific probe has a sequence of SEQ ID NO:15 and a ITPRIPL1 methylation specific probe has a sequence of SEQ ID NO:16.

In a further embodiment, the methods of the present disclosure further comprises a step of assaying the methylation level of the following one or more target DNA sequences or any of their combinations: C1orf114 or a fragment thereof, ZNF177 or a fragment thereof and C8orf47 or a fragment thereof. Furthermore, the methylation level of RKL001 is further assayed.

In some embodiments, a C1orf114 methylation specific probe, a ZNF177 methylation specific probe, or a C8orf47 methylation specific probe or any of their combinations is further used to assay the methylation level of the following one or more target DNA sequences or any of their combinations: C1orf114 or a fragment thereof, ZNF177 or a fragment thereof and C8orf47 or a fragment thereof. Further, the methylation specific probes of target C1orf114, ZNF177 and C8orf47 or fragments thereof have a sequence with homology of at least 85% to SEQ ID NOs:17, 18 and 14, respectively. In further embodiments, the methylation specific probes of target C1orf114 or a fragment thereof, ZNF177 or a fragment thereof and C8orf47 or a fragment thereof have a sequence of SEQ ID NOs:17, 18 and 14, respectively.

In some embodiments, the measure of the relative methylation status of the target C1orf114, ZNF177, and/or C8orf47 DNA sequences or fragments thereof compared to a control DNA sequence has higher than about 75% of sensitivity and about 76% specificity for C1orf114, and higher than about 62% of sensitivity and about 82% specificity for ZNF177, respectively. In some embodiments, the measure of the relative methylation status of the combination of target GCM2 and ITPRIPL1 or fragments thereof; target GCM2, ITPRIPL1 and C1orf114 or fragments thereof; and GCM2, ITPRIPL1, C1orf114 and ZNF177 or fragments thereof has higher than about 87% of sensitivity and about 96% specificity, higher than about 95% of sensitivity and about 72% specificity, higher than about 87% of sensitivity and about 96% specificity, respectively, compared to a control DNA sequence. In a further embodiment, the measure further comprises a step of measuring the specificity and sensitivity by a weighted sum score analysis. In some further embodiments, the measure of the relative methylation status of the combination of target GCM2, ITPRIPL1 and C1orf114 or fragments thereof or target GCM2, ITPRIPL1, C1orf114 and ZNF177 or fragments thereof has higher than about 87% of sensitivity and about 96% specificity and higher than about 91% of sensitivity and about 96% specificity, respectively.

In a further embodiment, an RKL001 methylation specific probe is further used to assay the methylation level of RKL001. Preferably, an RKL001 methylation specific probe has a sequence with homology of at least 85% to SEQ ID NO:13. More preferably, an RKL001 methylation specific probe has a sequence with homology of SEQ ID NO:13.

In some embodiments, the methylation status is detected by polymerase chain reaction, nucleic acid sequencing (such as bisulfite sequencing or pyrosequencing), bisulfite conversion, mass spectrometry, methylation specific nuclease, mass-based separation, target capture or microarray. In a particular embodiment, the methylation status is detected by polymerase chain reaction.

Certain embodiments of primers used in a polymerase chain reaction have a homology of about 85%, about 86%, about 87%, about 88%, about 89%, about 90%, about 91%, about 92%, about 93%, about 94%, about 95%, about 96%, about 97%, about 98%, about 99%, or higher percent to a sequence(s) selected from the group consisting of SEQ ID NOs: 1 to 12. In some embodiments, primers having sequences of SEQ ID NOs: 5 to 8 or probes having sequences of SEQ ID Nos: 15 and 16 are used to detect or measure the methylation status of the target DNA sequences GCM2 and ITPRIPL1 or fragments thereof.

The present disclosure also provides a kit for detecting and/or characterizing the methylation profile of epigenetic biomarkers in target DNA sequences as described herein. The kit can further comprise sodium bisulfite and adapters for whole target genes amplification, and polynucleotides (e.g., detectably-labeled polynucleotides) to quantify the presence of the converted methylated and or the converted unmethylated sequence of at least one cytosine from a DNA region of epigenetic biomarkers in target DNA sequences as described herein. Furthermore, the kit can further comprise methylation sensing restriction enzymes for whole target sequence or genes amplification.

In one embodiment, the kit further comprises one of more primers having sequences of SEQ ID NOs: 9 to 12 and 1 to 4 and/or one or more probes having sequences of SEQ ID Nos: 17, 18, 12 and 13 for assaying methylation status of epigenetic biomarkers in target DNA sequences GCM2 and ITPRIPL1 or fragments thereof in combination with one or more target DNA sequences C1orf114 or a fragment thereof, ZNF177 or a fragment thereof, C8orf47 or a fragment thereof, and RKL0014 or any of combinations thereof.

In one embodiment, the kit can be used for detecting and/or characterizing the methylation profile of epigenetic biomarkers in target DNA sequences GCM2 or a fragment thereof and ITPRIPL1 or a fragment thereof in combination with one or more target DNA sequences C1orf114 or a fragment thereof, ZNF177 or a fragment thereof, C8orf47 or a fragment thereof, and RKL0014 or any of combinations thereof. The kit further comprises one of more primers having sequences of SEQ ID NOs: 9 to 12 and 1 to 4 and/or one or more probes having sequences of SEQ ID Nos: 17, 18, 12 and 13 to detect or measure the methylation status of the target DNA sequences.

In a further embodiment, the kit further comprises methylation sensing restriction enzymes for whole target sequence or genes amplification.

DETAILED DESCRIPTION OF THE INVENTION

Figure 1:
FIGS. 1A to F show the heatmap for difference of methylation status of target nucleic acid and promoter, exon and gene body region of genes between tumor tissues and adjacent normal tissues, respectively (A: RKL001; B: C8orf47; C: GCM2; D: C1orf114; E: ITPRIPL1; F: ZNF177).
Figure 1:
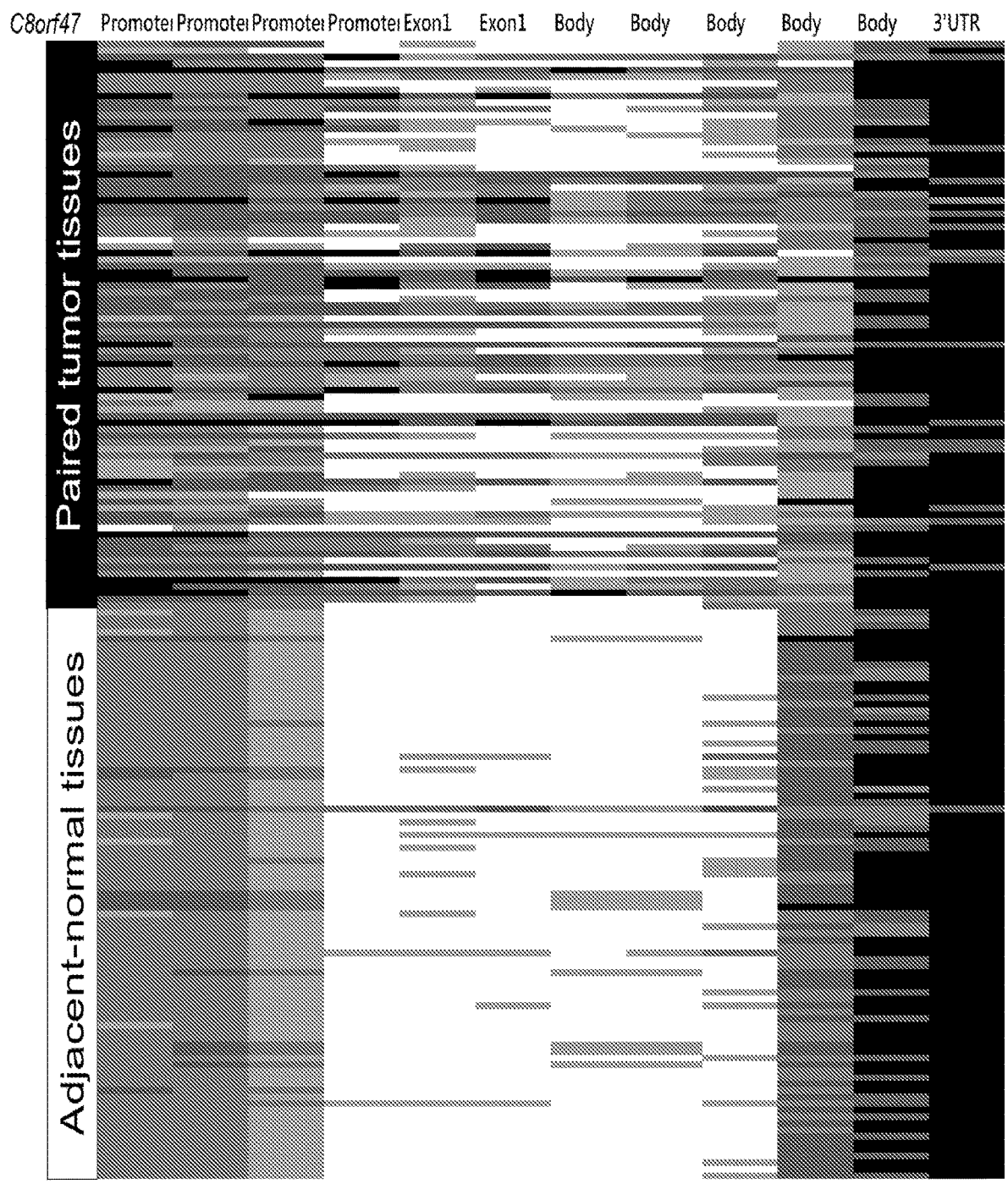
Figure 1:
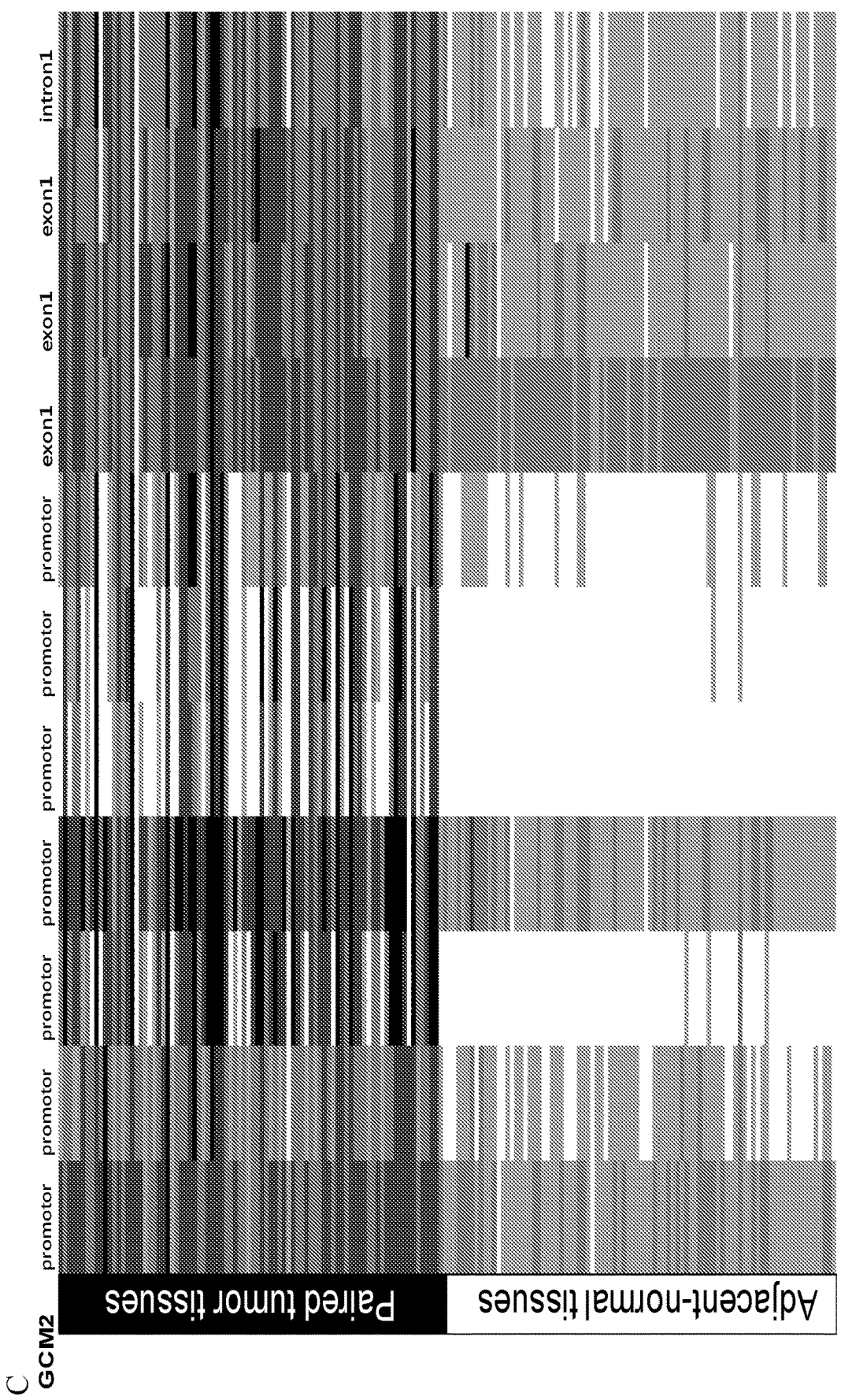
Figure 1:
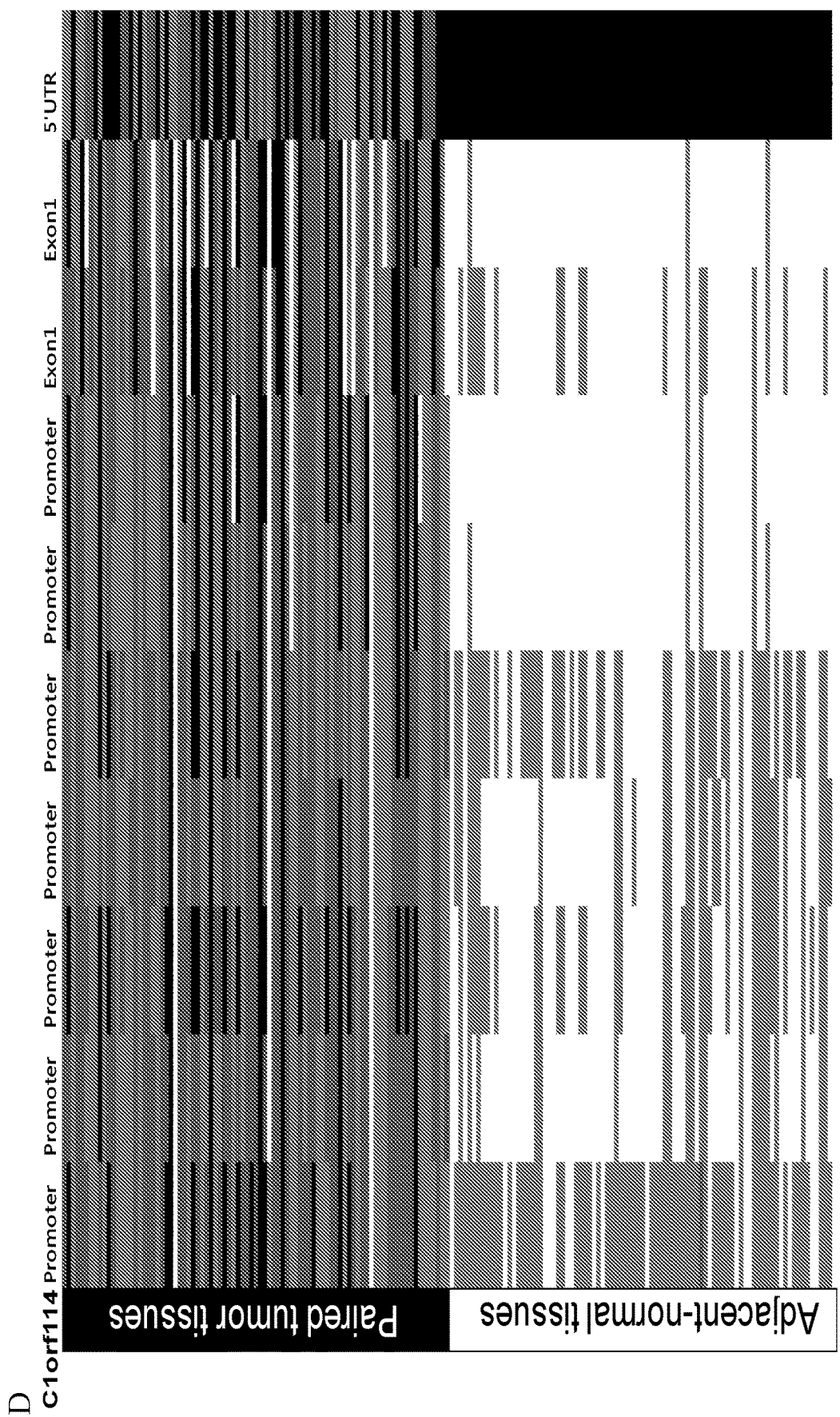
Figure 1:
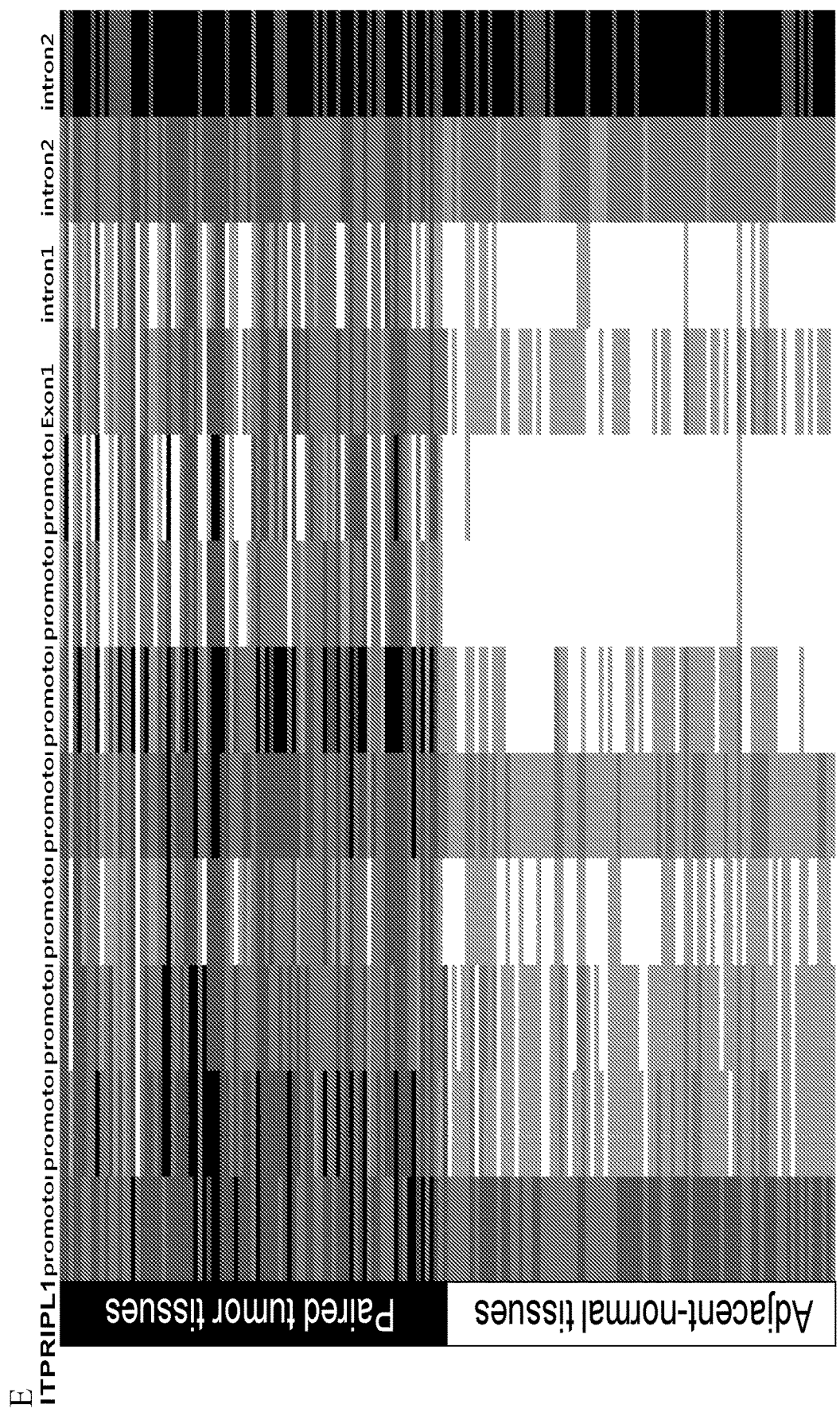
Figure 1:
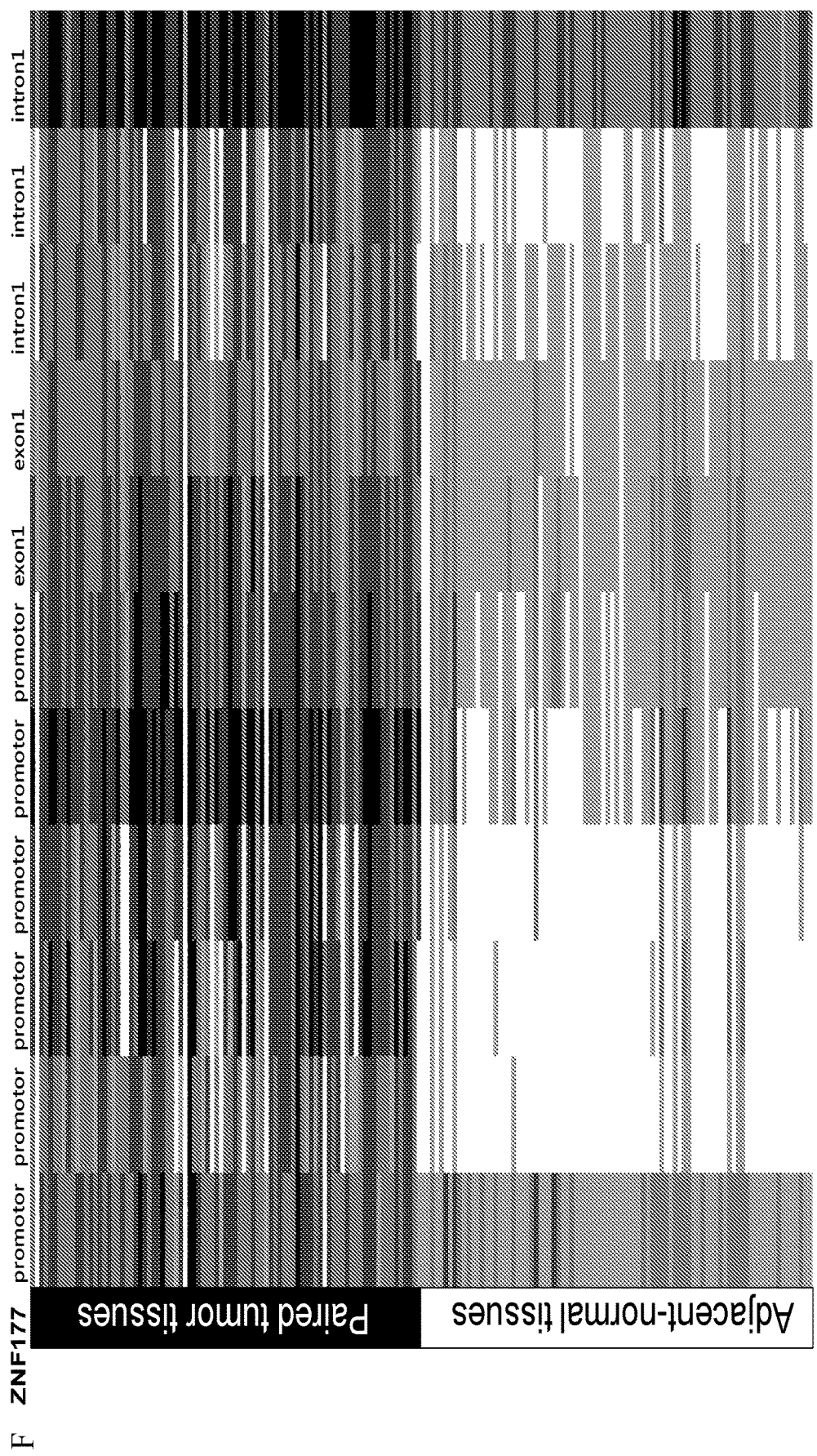

It is understood that this invention is not limited to the particular materials and methods described herein. It is also to be understood that the terminology used herein is for the purpose of describing particular embodiments and is not intended to limit the scope of the present invention, which will be limited only by the appended claims.

It must be noted that, as used in this specification and the appended claims, the singular forms "a," "an," and "the" include plural referents unless the content clearly dictates otherwise. Thus, for example, reference to "a biomarker" includes a mixture of two or more biomarkers, and the like.

The term "AUC" as used herein is an abbreviation for the area under a curve. In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5; for reference: J. P. Egan. Signal Detection Theory and ROC Analysis, Academic Press, New York, 1975).

The term "biological sample" refers to a sample of tissue, cells, or fluid isolated from a subject, including but not limited to, for example, blood, buffy coat, plasma, serum, blood cells (e.g., peripheral blood mononucleated cells (PBMCS), band cells, neutrophils, metamyelocytes, monocytes, or T cells), fecal matter, urine, bone marrow, bile, spinal fluid, lymph fluid, samples of the skin, external secretions of the skin, respiratory, intestinal, and genitourinary tracts, tears, saliva, milk, organs, biopsies and also samples of in vitro cell culture constituents, including, but not limited to, conditioned media resulting from the growth of cells and tissues in culture medium, e.g., recombinant cells, and cell components.

The term "biomarker" refers to a nucleic acid molecule which is present in a sample taken from patients having human cancer as compared to a comparable sample taken from control subjects (e.g., a person with a negative diagnosis or undetectable cancer, normal or healthy subject). The biomarker can be a nucleic acid, a fragment of a nucleic acid, a polynucleotide, or an oligonucleotide that can be detected and/or quantified. Biomarkers include polynucleotides comprising nucleotide sequences from genes.

The term "CpG island" as used herein refers to stretches of DNA in a genome that are rich in GC relative to the rest of the genome. Typically, the GC content is 50% or greater in these regions, which extend over hundreds of base pairs and sometimes thousands. Often these regions mark the 5' ends of genes.

A "control amount" of a biomarker can be any amount or a range of amount which is to be compared against a test amount of a biomarker.

As used herein, the term "early detection" of cancer refers to discovering the likelihood of cancer before metastasis. Preferably, it refers to discovering the likelihood of cancer before a morphological change in a sample tissue or cell is observed.

As used herein, the terms "detect", "detecting" or "detection" may describe either the general act of discovering or discerning or the specific observation of a detectably labeled composition.

The term "gene" refers to a nucleic acid (e.g., DNA) sequence that comprises coding sequences necessary for the production of a polypeptide, precursor, or RNA (e.g., non-coding RNAs such as ribosomal RNA, transfer RNA, splicosomal RNA, microRNA.). A polypeptide or non-coding RNA can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. Accordingly, a gene can include or exclude promoter sequences, terminators, translational regulatory sequences such as ribosome binding sites and internal ribosome entry sites, enhancers, silencers, insulators, boundary elements, replication origins, matrix attachment sites and locus control regions. The term also encompasses the coding region of a structural gene and the sequences located adjacent to the coding region on both the 5' and 3' ends for a distance of about 1 kb or more on either end such that the gene corresponds in length to the full-length mRNA. The term "gene" further includes both cDNA and genomic forms of a gene.

As used herein, the term "homology" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In some embodiments, the degree of homology between the two sequences is sufficient to allow homologous recombination therebetween, under appropriate stringent conditions.

Techniques for determining nucleic acid and amino acid sequence identity include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100.

In some embodiments, the degree of sequence similarity between polynucleotides can be determined by hybridization of polynucleotides under conditions that allow formation of stable duplexes between homologous regions, fol lowed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. See, e.g., Sambrook et al., supra; Nucleic Acid Hybridization: A Practical Approach, editors B. D. Hames and S. J. Higgins, (1985) Oxford; Washington, D.C.; IRL Press).

As used herein, the term "prediction" refers to the likelihood that a patient will respond either favorably or unfavorably to a drug or set of drugs, and also the extent of those responses. Thus, treatment predictive factors are variables related to the response of an individual patient to a specific treatment, independent of prognosis.

The term "methylation," as used herein, refers to the presence of a methyl group added by the action of a DNA methyl transferase enzyme to a cytosine base or bases in a region of nucleic acid, e.g., genomic DNA.

The term "methylation state," "methylation profile," or "methylation status" of a nucleic acid molecule refers to the presence or absence of one or more methylated nucleotide bases in the nucleic acid molecule. For example, a nucleic acid molecule containing a methylated cytosine is considered methylated (i.e., the methylation state of the nucleic acid molecule is methylated). A nucleic acid molecule that does not contain any methylated nucleotides is considered unmethylated.

The term "hypermethylation" refers to the average methylation state corresponding to an increased presence of methylated nucleotide bases in the nucleic acid molecule at one or a plurality of CpG dinucleotides within a DNA sequence of a test DNA sample, relative to the amount of methylated nucleotide bases in the nucleic acid molecule found at corresponding CpG dinucleotides within a normal control DNA sample.

The term "hypomethylation" refers to the average methylation state corresponding to a decreased presence of methylated nucleotide bases in the nucleic acid molecule at one or a plurality of CpG dinucleotides within a DNA sequence of a test DNA sample, relative to the amount of methylated nucleotide bases in the nucleic acid molecule found at corresponding CpG dinucleotides within a normal control DNA sample.

The term "subject" refers to humans.

The term "susceptibility" refers to a constitution or condition of the body which makes the tissues react in special ways to certain extrinsic stimuli and thus tends to make the individual more than usually susceptible to certain diseases.

The term "target site" or "target sequence" refers to a nucleic acid sequence that defines a portion of a nucleic acid to which a binding molecule will bind, provided sufficient conditions for binding exist.

The term "risk" refers to the estimated chance of getting a disease during a certain time period, such as within the next 10 years, or during the subject's lifetime.

The term "prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease.

The term "weight sum score" refers to every possible alternative being rated by a score including all objectives, individually weighted to stress the importance of different objectives.

Cancer is characterized by an abnormal growth of a cell caused by one or more mutations or modifications of a gene leading to dysregulated balance of cell proliferation and cell death. In many disease processes, such as cancer, gene promoter CpG islands acquire abnormal hypermethylation, which results in transcriptional silencing that can be inherited by daughter cells following cell division. DNA methylation causing silencing in cancer typically occurs at multiple CpG sites in the CpG islands that are present in the promoters of protein coding genes. Alterations of DNA methylation have been recognized as an important component of cancer development. DNA methylation profiling provides higher clinical sensitivity and dynamic range compared to other cancer detections. Accordingly, the present disclosure provides a method and kit for early prediction, treatment response and prognosis or recurrence monitoring of breast cancer.

In the present disclosure, the methylation status of GCM2 and ITPRIPL1 target DNA sequences or fragments thereof in a biological sample are measured to detect a breast cancer or detect a predisposition to, or the incidence of, a breast cancer or predict treatment response, prognosis or recurrence of a breast cancer in a human subject. In further embodiments, the methylation status of C1orf114, ZNF177 and/or C8orf47 target DNA sequences or fragments thereof in a biological sample are measured to detect a breast cancer or detect a predisposition to, or the incidence of, a breast cancer or predict treatment response, prognosis or recurrence of a breast cancer in a human subject. In a further embodiment, the methylation status of a nucleic acid sequence, RKL001, in human chromosome 19 is further measured.

GCM2 gene codes for glial cells missing homolog 2, which is thought to act as a binary switch between neuronal and glial cell determination. The GCM protein and mammalian GCM homologs contain a conserved N-terminal GCM motif that has DNA-binding activity. The GCM2 sequence and its function are known in the art such as described on the website: https://www.genecards.org/cgi-bin/carddisp.pl?gene=GCM2.

ITPRIPL1 gene codes from inositol 1,4,5-trisphosphate receptor interacting protein-like 1. The ITPRIPL1 sequence and its function are known in the art such as described on web site: https://www.genecards.org/cgi-bin/carddisp.pl?gene=ITPRIPL1.

ZNF177 codes for zinc finger protein 177. The ZNF177 sequence and its function are known in the art such as described on the website: https://www.genecards.org/cgi-bin/carddisp.pl?gene=ZNF177.

C8orf47 codes for glutamate rich protein 5. The C8orf47 sequence and its function are known in the art such as described on the website: https://www.genecards.org/cgi-bin/carddisp.pl?gene=ERICH5.

RKL001 is a nucleic acid sequence in chromosome 19, which has the following sequence:

(SEQ ID NO: 19)
CGCAGGCCAGGCCCTCTATTCCTGTCGCTGCGCCCCGCCTTGCCGGCTGC

GTGTCACCCCCCCCCCTGCCGCGCTGGCTCCCCGTCCGTCCCACCAGCCT

TGCTGTCCTGGGCAGGCCGGGGAATTCCTCCCGGTTCCTGGAAAAAACA.

In some embodiments, the methylation comprises a cytosine methylation site. In some instances, cytosine methylation comprises 5-methylcytosine (5-mCyt) and 5-hydroxymethylcytosine. In some cases, a cytosine methylation site occurs in a CpG dinucleotide motif In other cases, a cytosine methylation site occurs in a CHG or CHH motif, in which is adenine, cytosine or thymine. In some instances, one or more CpG dinucleotide motif or CpG site forms a CpG island, a short DNA sequence rich in CpG dinucleotide. In some instances, CpG islands are typically, but not always, between about 0.2 to about 1 kb in length. In some instances, the methylation comprises CpG island methylation.

In some embodiments, the methylation status is analyzed by a methylation specific enzymatic digest; bisulfite sequencing; an analysis selected from promoter methylation, CpG island methylation, MSP, HeavyMethyl, MethyLight, and Ms-SNuPE; and other methods relying on a detection of amplified DNA. The term "MethyLight™" refers to a fluorescence-based real-time PCR technique. MethyLight is described by Eads et al., Cancer Res. 59:2302-2306, 1999, herein incorporated by reference.

The term "HeavyMethyl" assay, refers to an assay wherein methylation specific blocking probes (also referred to herein as blockers) covering CpG positions between, or covered by the amplification primers enable methylation-specific selective amplification of a nucleic acid sample.

The term "Ms-SNuPE" refers to Methylation-sensitive Single Nucleotide Primer Extension. MsSNuPE is described by Gonzalgo & Jones, Nucleic Acids Res. 25:2529-2531, 1997, herein incorporated by reference.

The term "MSP" refers to Methylation-specific PCR. MSP is described by Herman et al. Proc. Natl. Acad. Sci. USA 93:9821-9826, 1996, and by U.S. Pat. No. 5,786,146, each of which are herein incorporated by reference.

Bisulfite modification of DNA is a method to assess CpG methylation status. 5-methylcytosine is the most frequent covalent base modification in the DNA of eukaryotic cells. However, 5-methylcytosine positions cannot be identified directly by sequencing or hybridization methods, because 5-methylcytosine has the same base pairing behavior as cytosine. Moreover, the epigenetic information carried by 5-methylcytosine is completely lost during, e.g., PCR amplification. Bisulfite sequencing is a method for analyzing DNA for the presence of 5-methylcytosine is based upon the specific reaction of bisulfite with cytosine whereby, upon subsequent alkaline hydrolysis, cytosine is converted to uracil which corresponds to thymine in its base pairing behavior. However, 5-methylcytosine remains unmodified under the aforementioned conditions. Thus, the original DNA is converted in such a manner that methylcytosine, which originally could not be distinguished from cytosine by its hybridization behavior, can be detected as the only remaining cytosine using molecular biological techniques, for example, by amplification and hybridization, or by sequencing.

In one embodiment, the methylation status is detected by polymerase chain reaction, nucleic acid sequencing (such as bisulfite sequencing or pyrosequencing), bisulfite conversion, mass spectrometry, methylation specific nuclease, mass-based separation, target capture or microarray. In one embodiment, the methylation status is detected by using primers to amplify a methylated CpG of the target genes. In a further embodiment, the detection of methylation is conducted by PCR, methylation specific PCR (MSP), real-time methylation specific PCR, quantitative methylation-specific PCR (QMSP), PCR using a methylated DNA-specific binding protein or quantitative PCR.

In one embodiment of the present disclosure, primer(s) that could amplify a methylated CpG of the genes described herein might be used. The primer(s) comprises at least one or more CpG dinucleotide in a region which hybridizes to the methylated CpG of the genes. Specifically, the primer(s) for amplifying a methylated CpG of the genes comprise sequence(s) having a homology of about 85%, about 86%, about 87%, about 88%, about 89%, about 90%, about 91%, about 92%, about 93%, about 94%, about 95%, about 96%, about 97%, about 98%, about 99%, or higher percent to sequence(s) selected from the group consisting of the following sequences.

| | |
|---|---|
| RKL001-qMSP-F | GTTTTTTATTTTTGTCGTTGCGTTTC (SEQ ID NO: 1) |
| RKL001-qMSP-R | CGAAAAAAATTCCCCGACCT (SEQ ID NO: 2) |
| C8orf47-qMSP-F | GTAGTTGTTTTCGGTTTTCGGTTTC (SEQ ID NO: 3) |
| C8orf47-qMSP-R | TACTATCGCCGACCTTATTAAAAACG (SEQ ID NO: 4) |
| GCM2-qMSP-F | GAGATAGGGCGGAGTTTTTC (SEQ ID NO: 5) |
| GCM2-qMSP-R | CTTAACCGCGATACTAAACGTT (SEQ ID NO: 6) |
| ITPRIPL1-qMSP-F | GAGTGTAGTTGATAGTAGGTACGGC (SEQ ID NO: 7) |
| ITPRIPL1-qMSP-R | GTAAATTTACTAAAAAAATAAAAAAACCGT (SEQ ID NO: 8) |
| C1orf114-qMSP-F | TTTTATTGGTTTTTCGTAAGTATCG (SEQ ID NO: 9) |
| C1orf114-qMSP-R | CATAACAACAACGTACCTCTACGTC (SEQ ID NO: 10) |
| ZNF177-qMSP-F | TTTAGTTGTTGGTCGGAAGC (SEQ ID NO: 11) |
| ZNF177-qMSP-R | CGACCTCACTAATAAAACGCA (SEQ ID NO: 12) |

Probe(s) capable of hybridizing with a methylated CpG of the genes described herein might be used. The probe(s) capable of hybridizing with a methylated CpG of the genes comprise at least one or more CpG dinucleotide in a region which hybridizes to the methylated CpG of the genes. Specifically, probe(s) might comprise sequence(s) having a homology of about 85%, about 86%, about 87%, about 88%, about 89%, about 90%, about 91%, about 92%, about 93%, about 94%, about 95%, about 96%, about 97%, about 98%, about 99%, or higher percent to sequence(s) selected from the group consisting of the following sequences.

| | |
|---|---|
| RKL001 qMSP probe | TGTCGCGTTGGTTTTTCGTTCGTTT (SEQ ID NO: 13) |
| C8orf47 qMSP probe | CTAAAACAACCCATTACGAAAAACGC (SEQ ID NO: 14) |
| GCM2 qMSP probe | GGTCGATGTTGTCGTTCGGGTGGA (SEQ ID NO: 15) |
| ITPRIPL1 qMSP probe | AGGGAGGTCGAGTAGCGGAGAGTGTG (SEQ ID NO: 16) |
| C1orf114 qMSP probe | TCGGGAGGGGTCGGTGGTTTGAG (SEQ ID NO: 17) |
| ZNF177 qMSP probe | GAAGTGGGCGTTCGTCGTTTCGTT (SEQ ID NO: 18) |

In one embodiment, the detection of the methylation status of the target genes comprises the presence of hypermethylation in the genes relative to a normal state of the target genes.

In some embodiments, the biological sample is a tissue, cell, blood, urine, serum or plasma from a patient suspected of having breast cancer or a subject to be detected.

As used herein, the term "a patient suspected of having cancer" refers to an individual who has received an initial diagnosis (e.g., a CT scan showing a mass or increased biomarker level) but for whom the stage of cancer or presence or absence of methylated genes indicative of cancer is not known. The term further includes people who once had cancer (e.g., an individual in remission).

In some embodiments, a detection test to correctly predict status is measured as the sensitivity of the assay, the specificity of the assay or the area under a receiver operated characteristic (ROC) curve (AUC). The greater the area under the ROC curve, for example, the more accurate or powerful the predictive value of the test.

In one embodiment, a weighted sum score is measured to determine the methylation status in the nucleic acid sequence and genes as an indicator. The weighted sum model (WSM) is the best known and simplest multi-criteria decision analysis (MCDA)/multi-criteria decision making method for evaluating a number of alternatives in terms of a number of decision criteria. According to the present disclosure, the weighted sum score analysis shows the combination of GCM2, ITPRIPL1, C1orf114 and ZNF177 shows a sensitivity higher than about 91% and a specificity higher than about 96% than the control.

In some embodiments, one or more of the biomarkers disclosed herein show a statistical difference in different samples of at least p<0.05. Detection tests that use these biomarkers may show an AUC of at least 0.9.

In some embodiments, the hypermethylation status of the epigenetic biomarkers in DNA sequences described herein correlates with a "poor" prognosis or the likelihood that a subject will likely respond unfavorably to a drug or set of drugs, leading to a progression of a cancer and/or to refractory of one or more therapeutic agents. In some instances, a "poor" prognosis refers to the likelihood that a subject will not respond to a drug or set of drugs, leading to a progression of a cancer. In some instances, a "poor" prognosis refers to the survival of a subject of from less than 5 years to less than 1 month. In some instances, a "poor" prognosis refers to the survival of a subject in which the survival of the subject upon treatment is from less than 5 years to less than 1 month. In some instances, a "poor" prognosis further refers to the likelihood that a subject will develop a refractory cancer toward one or more drugs.

In some embodiments, the present disclosure provides a kit for detecting and/or characterizing the methylation profile of the target DNA sequences described herein. In some embodiments, the target DNA sequences comprises the combination selected from the group consisting of: GCM2 and ITPRIPL1; GCM2, ITPRIPL1 and C1orf114; GCM2, ITPRIPL1, C1orf114 and ZNF177; GCM2, ITPRIPL1, C1orf114, ZNF177 and RKL1001; and GCM2, ITPRIPL1, C1orf114 and ZNF177, RKL1001 and C8orf47.

In some instances, the kit comprises a plurality of primers or probes to detect or measure the methylation status/levels of one or more target genes. Such kits comprise, in some instances, at least one polynucleotide that hybridizes to at least one of the methylation biomarker sequences described herein and at least one reagent for detection of gene methylation. Reagents for detection of methylation include, e.g., sodium bisulfate, polynucleotides designed to hybridize to sequence that is the product of a marker sequence if the marker sequence is not methylated (e.g., containing at least one C-U conversion), and/or a methylation-sensitive or methylation-dependent restriction enzyme. In some cases, the kits provide solid supports in the form of an assay apparatus that is adapted to use in the assay. In some instances, the kits further comprise detectable labels, optionally linked to a polynucleotide, e.g., a probe, in the kit. In some embodiments, the kit further comprises a process unit to obtain a weighted sum score as described herein.

Optionally, one or more detectably-labeled polypeptides capable of hybridizing to the amplified portion are also included in the kit. In some embodiments, the kits comprise sufficient primers to amplify the target DNA sequences described herein, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters for whole target genes amplification, and polynucleotides (e.g., detectably-labeled polynucleotides) to quantify the presence of the converted methylated and or the converted unmethylated sequence of at least one cytosine from a DNA region of an epigenetic biomarker described herein.

In some embodiments, the kits comprise methylation sensing restriction enzymes, primers and adapters for whole target genes amplification, and polynucleotides to quantify the number of copies of at least a portion of a DNA region of an epigenetic marker described herein. In some embodiments, the kits comprise a methylation binding moiety and one or more polynucleotides to quantify the number of copies of at least a portion of a DNA region of a marker described herein.

The inventions described and claimed herein have many attributes and embodiments including, but not limited to, those set forth or described or referenced in this Detailed Disclosure. It is not intended to be all-inclusive and the inventions described and claimed herein are not limited to or by the features or embodiments identified in this Detailed Disclosure, which is included for purposes of illustration only and not restriction. A person having ordinary skill in the art will readily recognize that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document, and should not be read as limiting the scope of the present invention. Any examples of aspects, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

Without further elaboration, it is believed that one skilled in the art can utilize the present invention to its fullest extent on the basis of the preceding description. The following examples are, therefore, to be construed as merely illustrative and not a limitation of the scope of the present invention in any way.

Although the present disclosure has been described with an exemplary embodiment, various changes and modifications may be suggested to one skilled in the art. It is intended that the present disclosure encompass such changes and modifications as fall within the scope of the appended claims.

EXAMPLE

Example 1

Methylation Status of Target Nucleic Acid and Genes of in Breast Cancer Tissue

The β value for Illumina Methylation 450K array-based data was generated from The Cancer Genome Atlas (TCGA) Research Network. The target nucleic acid and genes were selected when β value from normal tissues is less than 0.15; Δβ value (the value of Tumor subtracts that of normal tissues) is higher than 0.3. The Δβ value of GCM2, ITPRIPL1, C1orf114 and ZNF177, RKL1001 and C8orf47 is much higher than 0.3.

| Breast Cancer | |
|---|---|
| | β value (T) |
| GCM2 | 0.70 |
| ITPRIPL1 | 0.76 |
| C1orf114 | 0.77 |
| ZNF177 | 0.70 |
| RKL001 | 0.52 |
| C8orf47 | 0.49 |

β value (T), methylation level of tumor tissues;
β value (T) > 0.3 that labeled blue will be calculated as biomarkers for other cancers.

FIG. 1 shows the difference of methylation status (β value) of target nucleic acid and genes between tumor tissues and adjacent normal tissues (n=97). Darker color indicates tissues with higher methylation status according to Illumina Methylation 450K array-based data.

Example 2

Detection of Difference of Methylation Status Between the Target Nucleic Acid and Genes of in Breast Cancer Tissue and Normal Tissue Genomic DNA from matched pairs of primary tumors and adjacent breast tissues from the same patient from breast cancer patients were extracted and followed by bisulfite conversion. The methylation specific real-time PCR (qMSP) was used in detection of DNA methylation analyses in breast tumor tissues and adjacent normal tissues. The ACTB gene was used as a reference gene. Targets as considered hypermethylated when the methylation level of target genes relative to that of the ACTB gene was at least 2-fold higher in the breast tumor compared with the paired normal breast tissue sample. All the hypermethylation rate in breast tumors compared to adjacent normal tissues of GCM2, ITPRIPL1, C1orf114 and ZNF177, RKL1001 and C8orf47 is higher than 64%.

| Breast Cancer | |
|---|---|
| Gene Name | Hypermethylation status No./Total patients(%) |
| GCM2 | 63/91 (69%) |
| ITPRIPL1 | 73/91 (80%) |
| C1orf114 | 71/91 (78%) |
| ZNF177 | 71/91 (78%) |
| RKL001 | 45/69 (65%) |
| C8orf47 | 54/83 (65%) |

Example 3

Early Detection of Methylation Status of Epigenetic Biomarkers of Target Genes in Plasma Samples of Healthy Subjects and Breast Cancer Patients The circulating cell-free DNA was extracted from plasma. Briefly, 3.5 mL of plasma was isolated immediately from 10 mL of peripheral blood. After circulating cell-free DNA (cfDNA) was extracted from plasma that obtained from 24 breast cancer patients and 25 healthy subjects, cfDNA was performed by bisulfite conversion. Probe-based methylation specific real-time PCR (qMSP) was used for cfDNA methylation analyses. The early prediction by GCM2, ITPRIPL1, C1orf114 and ZNF177 revealed 91.7% sensitivity and 96.0% specificity (AUC: 0.954).

| | Sensitivity | Specificity | AUC |
|---|---|---|---|
| GCM2 | 54.2% | 100% | 0.771 |
| ITPRIPL1 | 79.2% | 96.2% | 0.877 |
| C1orf114 | 75.0% | 76.9% | 0.760 |
| ZNF177 | 62.5% | 82.6% | 0.736 |
| GCM2 + ITPRIPL1 | 87.5% | 96% | 0.927 |
| GCM2 + ITPRIPL1 + C1orf114 | 95.8% | 72.0% | 0.944 |
| GCM2 + ITPRIPL1 + C1orf114 (after weighted sum score analysis) | 87.5% | 96.7% | 0.981 |
| GCM2 + ITPRIPL1 + C1orf114 + ZNF177 | 87.5% | 96.0% | 0.947 |
| GCM2 + ITPRIPL1 + C1orf114 + ZNF177 (after weighted sum score analysis) | 91.7% | 96.0% | 0.954 |
| CA153 | 0% | 100% | 0.500 |
| CEA | 12.5% | 100% | 0.563 |

Figure 2:
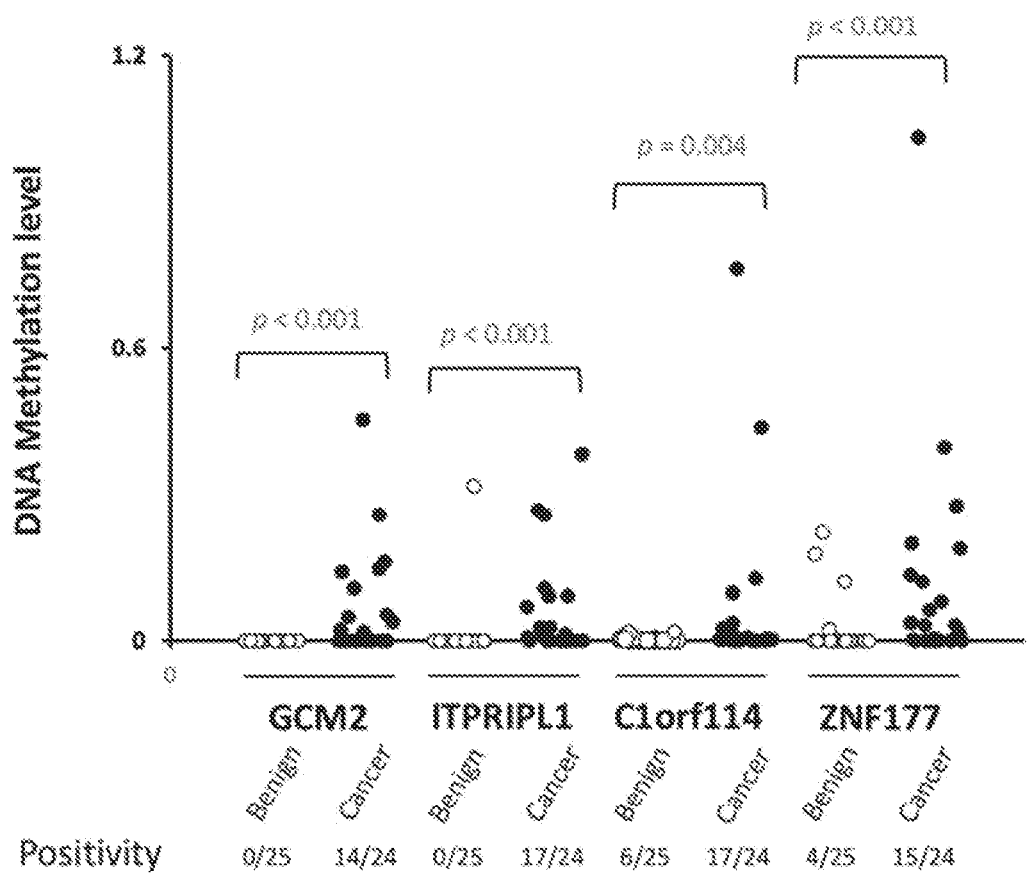
FIG. 2 shows the difference in early detection of the methylation status of epigenetic biomarkers of target genes in plasma samples of healthy subjects and breast cancer patients.
Figure 3:
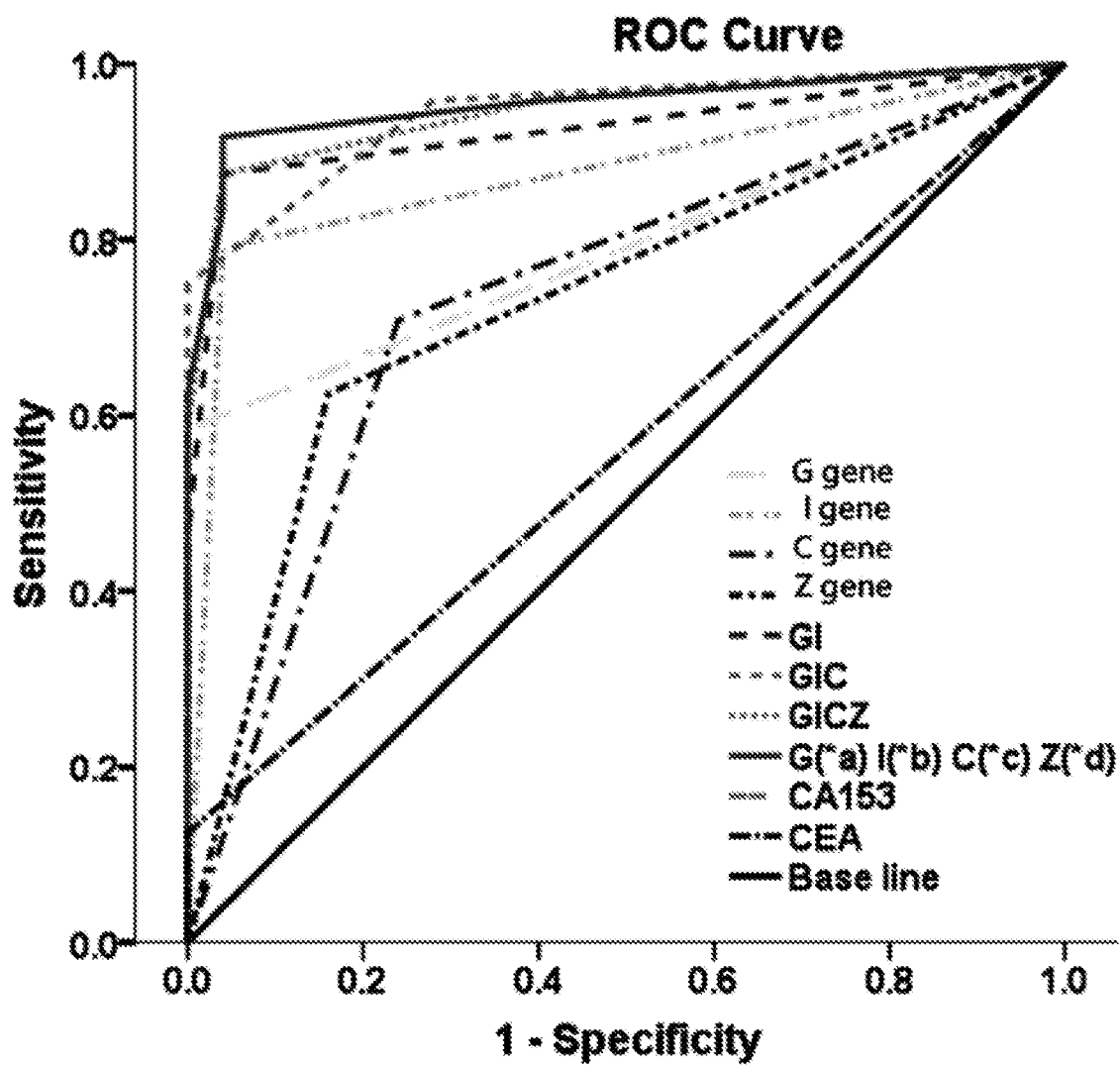
FIG. 3 shows Receiver Operating Characteristic (ROC) Curve Analysis exhibiting the early detection of the methylation status of epigenetic biomarkers of target genes in breast cancer patients and healthy subjects. GI: GCM2, ITPRIPL1; GIC: GCM2, ITPRIPL1, C1orf114; GICZ: GCM2, ITPRIPL1, C1orf114, ZNF177; G(a*) I(b*) C(c*) Z(d*): GCM2+ITPRIPL1+C1orf114+ZNF177 after weighted sum score analysis.

FIG. 2 shows the difference in early detection of the methylation status of epigenetic biomarkers of target genes in plasma samples of healthy subjects and breast cancer patients. In addition, Receiver Operating Characteristic (ROC) Curve Analysis as shown in FIG. 3 indicates the early detection of the methylation status of epigenetic biomarkers of target genes in breast cancer patients and healthy subjects.

Example 4

Figure 4:
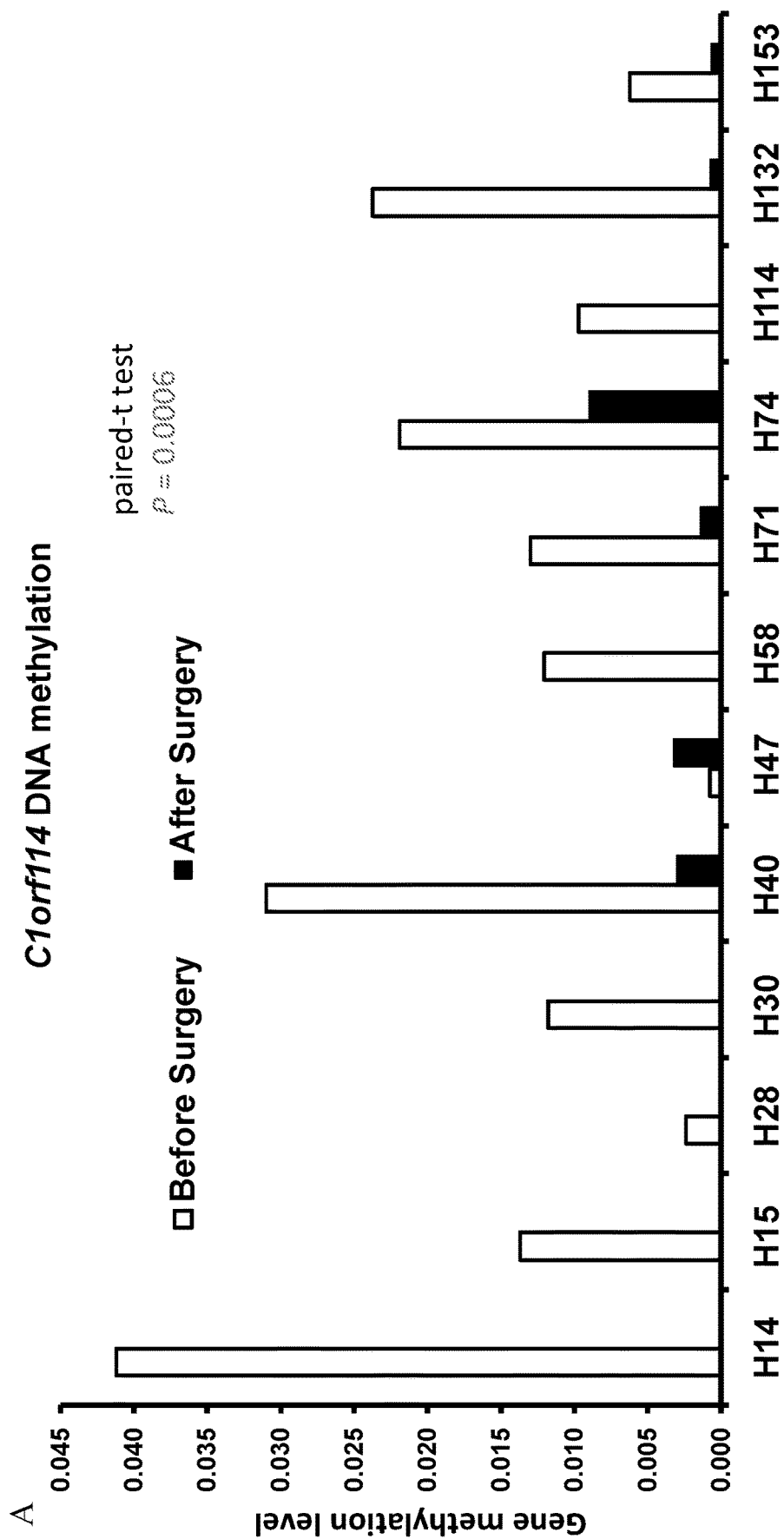
FIGS. 4A to C show the treatment response through the methylation status of epigenetic biomarkers of target genes C1orf114 (A), CA-153 (B) and CEA (C) in breast cancer patients before and after surgery.
Figure 4:
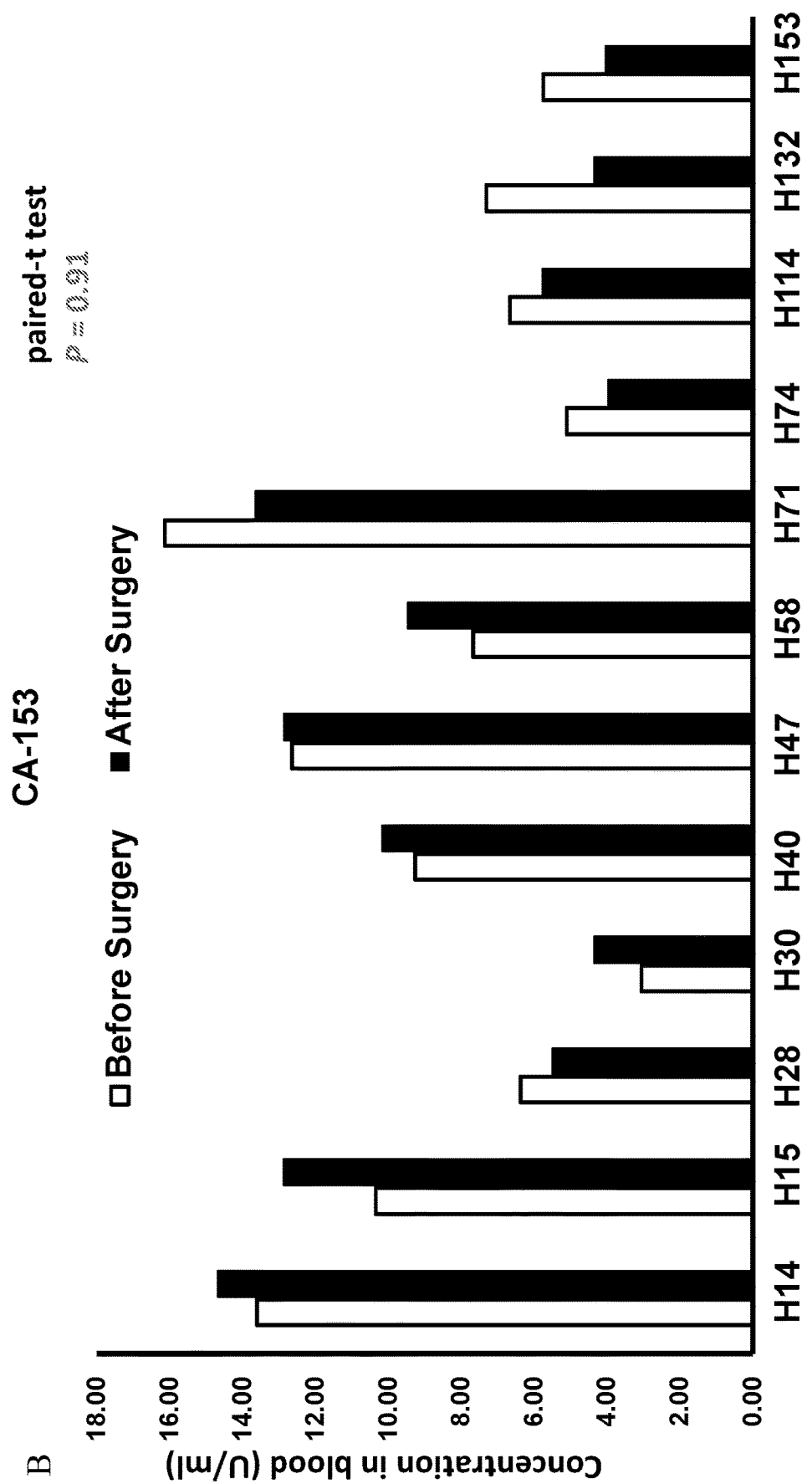
Figure 4:
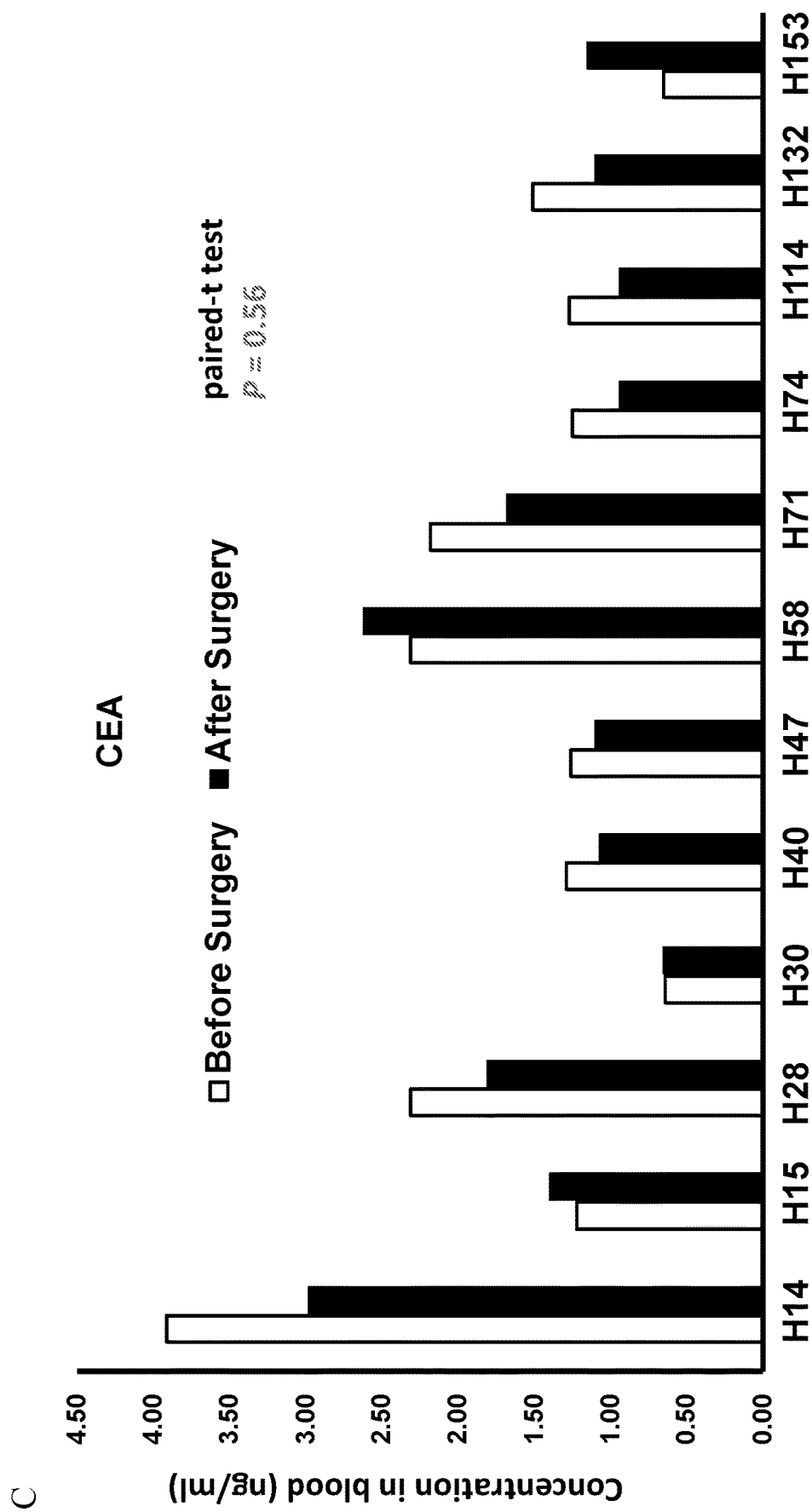

Treatment Response Monitored by Methylation Status of Epigenetic Biomarkers of Target Genes in Breast Cancer Patients The cfDNA from plasma of breast cancer patients were analyzed by Probe-based methylation specific real-time PCR (qMSP). CA-153 and CEA tumor marker are the current clinical use cancer biomarkers, which were used as comparative markers. The results show methylation status of epigenetic biomarkers can sensitively response to medical surgery treatment. As shown in FIG. 4, the treatment response through the methylation status of epigenetic biomarkers of target genes in breast cancer patients before and after surgery.

Example 5

Figure 5:
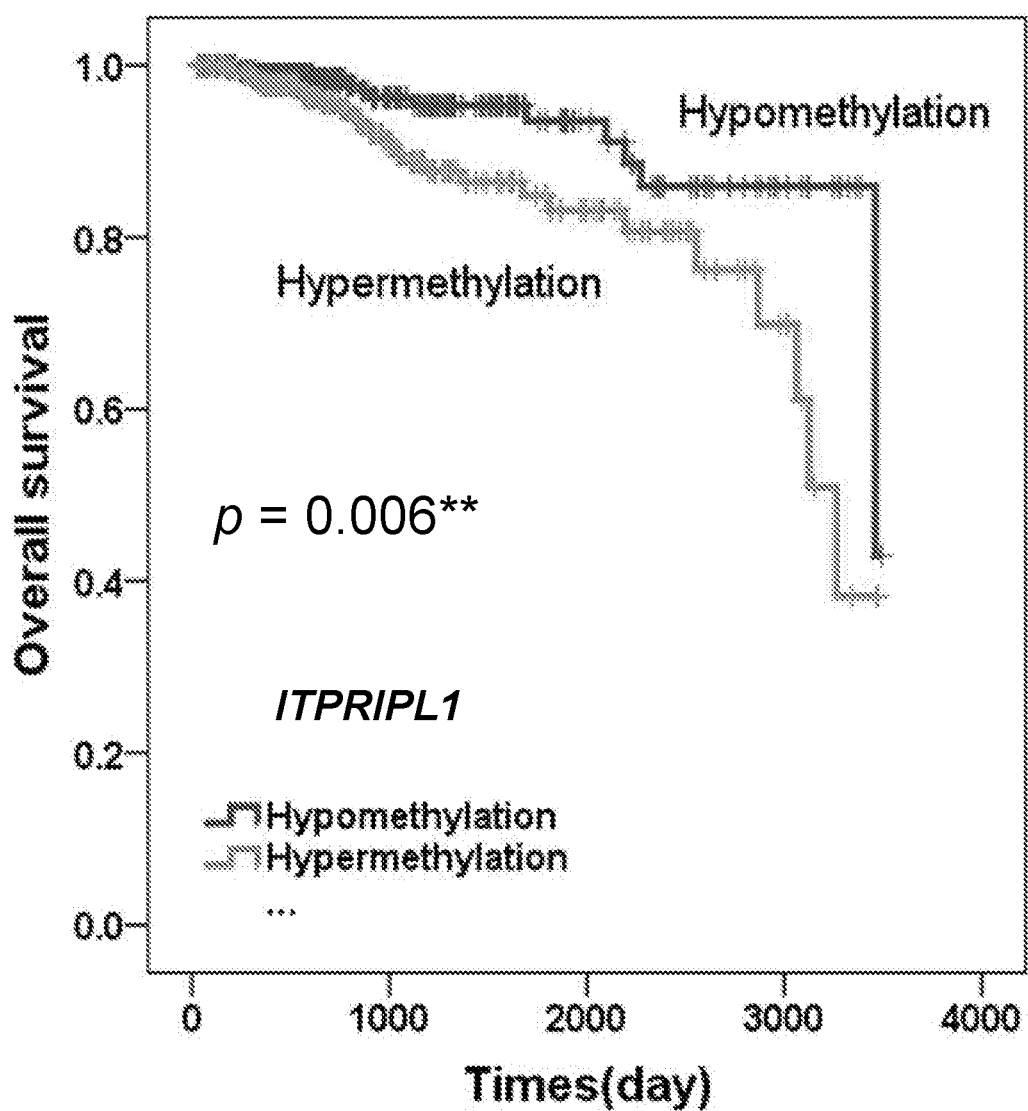
FIG. 5 shows poor prognosis in breast cancer patients based on the Kaplan-Meier curve of the methylation status of ITPRIPL1 gene.

Prognosis Prediction by Methylation Status of Epigenetic Biomarkers of Target Genes in Breast Cancer Patients Illumina Methylation 450K array-based data and followed-up information were generated from The Cancer Genome Atlas (TCGA) Research Network. The overall survival curves were calculated using the Kaplan-Meier method, and comparisons were performed using the log-rank and Wilcoxon test by SPSS software (SPSS Inc., Chicago, IL, USA). The Kaplan-Meier curve shown in FIG. 5 indicates the methylation status of ITPRIPL1 gene had poor prognosis in breast cancer patients. The overall survival curves GCM2, ITPRIPL1, C1orf114, ZNF177, C8orf47 and/or RKL1001 and/or any of their combinations were also calculated using the Kaplan-Meier method.

What is claimed is:

1. A method for determining an increased risk of breast cancer in a human subject, wherein the method comprises:
   (a) providing (i) a biological sample containing DNA from the human subject and extracting cell-free DNA from the sample or (ii) a biological sample from a breast tumor tissue of the human subject and extracting the genomic DNA from the sample, wherein the cell-free DNA or the genomic DNA comprises the targets of GCM2 and ITPRIPL1 DNA;
   (b) assaying methylation level of the GCM2 and ITPRIPL1 from the cell-free DNA sample or the genomic DNA sample using methylation specific polymerase chain reaction assay (MSP), wherein the forward and reverse primers used in the assay comprise SEQ ID NO: 5-6 for GCM2 and SEQ ID NO: 7-8 for ITPRIPL1:
GCM2 forward primer: GAGATAGGGCGGAGTTTTC (SEQ ID NO:5)
GCM2 reverse primer: CTTAACCGCGATACTAAACGTT (SEQ ID NO:6)
ITPRIPL1 forward primer: GAGTGTAGTTGATAGTAGGTACGGC (SEQ ID NO:7)
ITPRIPL1 reverse primer: GTAAATTTACTAAAAAAATAAAAAAACCGT (SEQ ID NO:8);
(c) comparing the methylation levels of Step (b) to methylation levels from a control sample without breast cancer; and
(d) determining an increased risk of breast cancer in the human subject based upon a higher methylation level detected in the sample as compared to the control sample.

2. The method of claim 1, wherein a GCM2 methylation specific probe and a ITPRIPL1 methylation specific probe are used in the assay.

3. The method of claim 1, wherein the methylation in the target is
about 64% higher than that of the control sample; or
about 69% and about 80%, respectively, higher than that of the control sample.

4. The method of claim 2, wherein:
(i) the GCM2 methylation specific probe has a sequence with a homology of at least 85% to SEQ ID NO:15, and the ITPRIPL1 methylation specific probe has a sequence with a homology of at least 85% to SEQ ID NO:16; or (ii) the GCM2 methylation specific probe has a sequence of SEQ ID NO:15, and the ITPRIPL1 methylation specific probe has a sequence of SEQ ID NO:16.

5. A method for determining an increased risk of breast cancer in a human subject, wherein the method comprises:
(a) providing (i) a biological sample containing DNA from the human subject and extracting cell-free DNA from the sample or (ii) a biological sample from a breast tumor tissue of the human subject and extracting the genomic DNA from the sample, wherein the cell-free DNA or the genomic DNA comprises the targets of GCM2 and ITPRIPL1 DNA,
(b) assaying methylation levels of the GCM2 and ITPRIPL1 from the cell-free DNA sample or the genomic DNA sample using methylation specific polymerase chain reaction assay (MSP), wherein the probes used in the assay comprises SEQ ID NO: 15 for GCM2 and SEQ ID NO: 16 for ITPRIPL1;
(c) comparing the methylation levels of Step (b) to methylation levels from a control sample without breast cancer; and
(d) determining an increased risk of breast cancer in the human subject based upon a higher methylation level detected in the sample as compared to the control sample.

6. The method of claim 5, wherein the following forward and reverse primers are further used in the assay:
GCM2 forward primer: GAGATAGGGCGGAGTTTTC (SEQ ID NO:5); GCM2 reverse primer: CTTAACCGCGATACTAAACGTT (SEQ ID NO:6); ITPRIPL1 forward primer: GAGTGTAGTTGATAGTAGGTACGGC (SEQ ID NO:7); ITPRIPL1 reverse primer: GTAAATTTACTAAAAAAATAAAAAAACCGT (SEQ ID NO:8).

* * * * *